United States Patent [19]

Liu et al.

[11] 4,447,533
[45] May 8, 1984

[54] PROCESS TO PRODUCE ANTIBIOTIC X-14885A

[75] Inventors: Chao-Min Liu, Cedar Grove, N.J.; Homer D. Tresner, LaFarge, Wis.; John Westley, Cedar Grove, N.J.

[73] Assignee: Hoffmann-La Roche Inc., Nutley, N.J.

[21] Appl. No.: 403,844

[22] Filed: Jul. 30, 1982

Related U.S. Application Data

[62] Division of Ser. No. 311,132, Oct. 14, 1981, Pat. No. 4,352,934.

[51] Int. Cl.³ .................... C12P 17/18; C12R 1/465
[52] U.S. Cl. ........................... 435/119; 435/886
[58] Field of Search ................... 435/119, 886

[56] References Cited

U.S. PATENT DOCUMENTS 3,923,823  12/1975  Gale et al. ............. 435/119 X
4,368,265   1/1983  Liu ....................... 435/119 X Primary Examiner—Robert J. Warden
Attorney, Agent, or Firm—Jon S. Saxe; Bernard S. Leon; Frank P. Hoffman

[57] ABSTRACT

There is presented an antibiotic compound of the formula

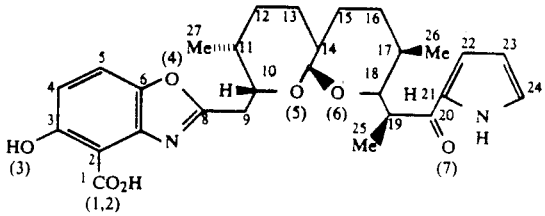

and the pharmaceutically acceptable salts and esters thereof.

The compound exhibits activity as an anti-swine dysentery agent and an antimicrobial agent.

Also presented is a fermentation process to produce the compound of formula I.

1 Claim, No Drawings

PROCESS TO PRODUCE ANTIBIOTIC X-14885A

This is a division of application Ser. No. 311,132 filed Oct. 14, 1981, now U.S. Pat. No. 4,352,934.

DESCRIPTION OF THE INVENTION

The present invention relates to an antibiotic compound of the formula

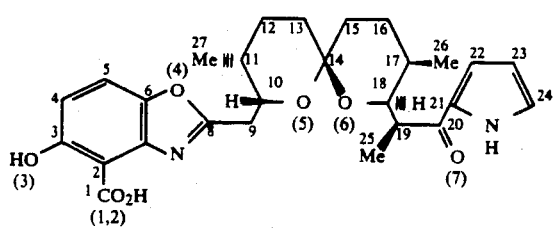

and the pharmaceutically acceptable salts and esters thereof.

The compound of formula I is produced by a fermentation process utilizing a newly discovered organism designated Streptomyces sp. X-14885. A culture of the living organism designated as X-14885 has been deposited at the Northern Regional Research Laboratories, Peoria, Ill. and added to its permanent collection of microorganisms as NRRL 12350.

The microorganism was isolated from a soil sample collected at Dead Indian Creek, Wyo.

GENERAL CHARACTERISTICS

Strain X-14885 produces a substrate mycelium which does not fragment into spores and aerial mycelium forming retinaculum-apertum spore chains with approximately twenty-five (25) spores per chain. Spores could not be differentiated under the scanning electron microscope. The surface of the spore chain appears to be smooth. The cell wall contains the LL-isomer of diaminopimelic acid which together with the above characteristics places this organism in the genus Streptomyces.

GROWTH CHARACTERISTICS

The standard ISP media set forth in Shirling and Gottlieb, "Methods for Characterization of Streptomyces Species", Intern. J. System. Bacteriol., 16, pp. 313-400, 1966, as well as various other media used to characterize the culture are listed below:

ISP-1 through ISP-9 are described by Shirling and Gottlieb in above article.

Czapek-Dox: Czapek-Dox Broth (BBL) to which 1.5% agar was added;

Sodium chloride tolerance, reduction of nitrate and hydrolysis of casein media are described in "Rapidly Growing Acid Fast Bacteria", J. Bacteriol., 66, 41-48, 1953;

Decomposition of adenine, xanthine, tyrosine and hypoxanthine media as described in "The Taxonomy of Soil Bacteria" in "Ecology of Soil Bacteria", Liverpool University Press, pp. 293-321, 1967;

Gelatin media as described in "A Guide to Identification of the Genera of Bacteria", The Williams and Wilkins Co., Baltimore, 1967 modified with nutrient gelatin (BBL) plus 2.0% agar in place of meat infusion agar plus gelatin; and Starch Media (Actinomyces broth (Difco) plus 0.25% soluble starch and 2.0% agar).

Table 1 below describes the amount of growth, degree of sporulation, spore mass color and color of the reverse substrate mycelium on various agar media.

TABLE 1

| Agar Medium | Amount of Growth Degrees of Sporulation | Spore Mass Color[a] | Color of Reverse Substrate Mycelium |
|---|---|---|---|
| Yeast plus malt extract (ISP2) | moderate growth; sparse sporulation | [b](oyster white) in isolated tufts; 2ge (covert tan) on the rest where not sporulated | 2ge (covert tan) |
| Oatmeal (ISP3) | poor growth; no sporulation | 2cb (ivory tint) not sporulated | 2dc (natural, string) |
| Inorganic salts-starch (ISP4) | poor growth; no sporulation; does not appear to hydrolyze starch in medium | 2cb (ivory tint) | 2dc (natural, string) |
| Glycerol-Asparagine (ISP5) | poor growth; very scant sporulation | 2cb (ivory tint) | 2dc (natural, string) |
| Czapek-Dox[b] | poor growth; almost no sporulation | translucent 2cb (ivory tint) | 2dc (natural, string) |

[a]The color scheme used was that taken from the Color Harmony Manual, 4th ed., 1958 (Container Corp. of America, Chicago).
[b]Czapek-Dox broth (BBL) to which 1.5% agar was added.

Streptomyces sp. X-14885 hydrolyzes casein, starch, gelatin but not urea. It decomposes adenine, hypoxanthine and tyrosine but not xanthine. Table 2 below compares the carbon utilization characteristics of Streptomyces sp. X-14885 with those of *Streptomyces humidus* and *Streptomyces lusitanus* chosen for comparison since they appeared to be the closest relatives based on gray spore mass color, smooth spores in a spiral to retinaculum-apertum spore chain, lack of melanin and a similar but not identical carbon utilization pattern.

TABLE 2

| | Comparison of Carbon Utilization by Strain X-14885 and Related Strains | | | |
|---|---|---|---|---|
| | Result[a] in this laboratory | | | Result reported in Bergey's Manual[b] |
| Carbon source | X-18445 | S. humidus | S. lusitanus | S. lusitanus |
| No carbon control | − | − | − | − |
| D-Glucose | ++ | ++ | ++ | + |
| D-Xylose | ± | + | − | − |

TABLE 2-continued
Comparison of Carbon Utilization by
Strain X-14885 and Related Strains

| Carbon source | Result[a] in this laboratory | | | Result reported in Bergey's Manual[b] |
|---|---|---|---|---|
| | X-18445 | S. humidus | S. lusitanus | S. lusitanus |
| L-Arabinose | ± | ++ | − | ± |
| L-Rhamnose | ++ | ++ | − | − |
| D-Fructose | ± | ++ | − | + |
| D-Galactose | + | ++ | + | |
| Raffinose | − | − | − | − |
| D-Mannitol | − | ++ | − | − |
| i-Inositol | + | +(+) | − | ± |
| Salicin | + | + | ± | − |
| Sucrose | − | − | − | + |
| Cellulose | − | − | − | |

[a] —: Negative response; ±: doubtful response; +: more growth than carbon control but less than on glucose; +(+): growth nearly equal to amount on glucose; and ++: positive response equal to growth on glucose.
[b] Buchanan, R. E. and N. E. Gibsons (Ed.), Bergey's Manual of Determinative Bacteriology, 8th Ed., p. 772 (1974).

Table 3 below sets forth the morphological and metabolic characteristics of Streptomyces sp. X-14885.

TABLE 3

| Metabolic and Morphological Characteristics | |
|---|---|
| Test | Results |
| Spore mass color | gray-white |
| Spore chain form | Retinaculum-apertum |
| ISP6, darkening | − |
| Melanin, ISP7 | − |
| ISP1, darkening | − |
| Gelatin hydrolysis | + |
| Casein hydrolysis | + |
| Starch hydrolysis | + |
| NaCl (%) tolerance | 3 |
| Growth range temp (°C.) | 10–28 |
| Reverse-side pigment | none |
| Soluble pigment | none |
| Stretomycin sensitivity (10 μg disc) | +9 mm |
| Nitrate reduction | ±slight |
| Hygroscopic property | − |
| DAP isomer | LL |

The species Streptomyces sp. X-14885 described herein includes all strains of Streptomyces which form a compound of formula I and which cannot be definitely differentiated from the culture number X-14885 and its subcultures including mutants and variants. The compound of formula I is identified herein and after this identification is known, it is easy to differentiate the strains producing a compound of formula I from others.

Streptomyces sp. X-14885, when grown under suitable conditions, produces a compound of formula I. A fermentation broth containing Streptomyces sp. X-14885 is prepared by inoculating spores or mycelia of the organism producing the compound of formula I into a suitable medium and then cultivating under aerobic conditions. For the production of a compound of formula I, cultivation on a solid medium is possible but for production in large quantities, cultivation in a liquid medium is preferable. The temperature of the cultivation may be varied over a wide range, 20°–35° C., within which the organism may grow but a temperature of 26°–30° C. and a substantially neutral pH are preferred. In the submerged aerobic fermentation of the organism for the production of a compound of formula I, the medium may contain as the source for carbon, a commercially available glyceride oil or a carbohydrate, such as, glycerol, glucose, maltose, lactose, dextrin, starch, etc. in pure or crude states and as the source of nitrogen, an organic material, such as, soybean meal, distillers' solubles, peanut meal, cotton seed meal, meat extract, peptone, fish meal, yeast extract, corn steep liquor, etc. and when desired inorganic sources of nitrogen, such as, nitrates and ammonium salts and mineral salts, such as, ammonium sulfate, magnesium sulfate and the like. It also may contain sodium chloride, potassium chloride, potassium phosphate and the like and buffering agents, such as, sodium citrate, calcium carbonate or phosphates and trace amounts of heavy metal salts. In aerated submerged culturing procedures, an anti-foam agent, such as, liquid paraffin, fatty oils or silicone compounds is used. More than one kind of carbonate source, nitrogen source or anti-foam source may be used for production of a compound of formula I.

The pharmaceutically acceptable salts of the compound of formula I can be prepared by conventional means. These salts are prepared from the free acid form of the antibiotic by methods well-known in the art, for example, by washing the free acid in solution with a suitable base or salt. Examples of such pharmaceutically acceptable basic substances capable of forming salts for the purpose of the present invention include alkali metal bases, such as, sodium hydroxide, potassium hydroxide, lithium hydroxide and the like; alkaline earth metal bases, such as, calcium hydroxide, barium hydroxide and the like; and ammonium hydroxide. Alkali metal or alkaline earth metal salts suitable for forming pharmaceutically acceptable salts can include anions, such as, carbonates, bicarbonates and sulfates.

Esters of the compound of formula I can be prepared by conventional means known in the art.

The following examples will serve to illustrate the invention without limiting it thereto.

EXAMPLE 1

Tank fermentation

The Streptomyces X-14885 culture is grown and maintained on a yeast extract-malt extract agar slant having the following composition (grams/liter distilled water):

| Yeast extract (Difco) | 4.0 |
|---|---|
| Malt extract (Difco) | 10.0 |
| Dextrose | 4.0 |
| Agar | 15.0 | pH is adjusted to 7.3 with NaOH before autoclaving.

The slant is inoculated with X-14885 culture and incubated at 28° C. for 7–14 days. A chunk of agar containing spores and mycelia from the sporulated culture slant is used to prepare vegetative inoculum by inoculating a 6-liter Erlenmeyer flask containing 2 liters of inoculum medium having the following composition (grams/liter distilled water):

| Tomato pomace | 5.0 |
|---|---|
| Distillers soluble | 5.0 |
| OM peptone | 5.0 |
| Debittered yeast | 5.0 |
| Cornstarch | 20.0 |
| CaCO$_3$ | 1.0 |
| K$_2$HPO$_4$ | 1.0 |
| CoCl$_2$ | 0.00013 | pH is adjusted to 7.0 with NaOH before sterilization.

The inoculated medium is incubated for 96 hours at 28° C. on a rotary shaker operating at 250 rpm, 2-inch stroke.

Four liters of this culture are used to inoculate 60 gallons of the following medium in a 100-gallon fermentor (grams/liter tap water):

| | |
|---|---|
| Cerelose | 45.0 |
| Eclipse N starch | 20.0 |
| Soyalose 105 | 15.0 |
| Black strap molasses | 3.0 |
| Hydrolyzed fish protein (Louisiana Marine Protein Inc.) | 10.0 |
| Soybean oil | 10.0 |
| $CaCO_3$ | 2.5 |
| $CoCl_2$ | 0.00013 |
| SAG 4130 Anti-foam (Union Carbide) | 0.1 |

The pH of the medium is adjusted to 7.0 with NaOH before sterilization for 1¼ hours with 60 lb/in² steam. The fermentation is carried out at 28° C. for 164 hours. The inoculated medium is aerated with compressed air at a rate of 3 cubic feet per minute and is stirred with agitator at 280 rpm. The fermentation is carried out at 28° C. for 164 hours.

EXAMPLE 2

Isolation of Antibiotic X-14885-Na Salt from Tank Fermentation of Streptomyces Culture X-14885

Step A. To the whole broth from a sixty-two gallon (235 liters) fermentation, after 164 hours growth, an equal volume of ethyl acetate was added at pH=10.0. After stirring for one hour, the solvent layer was separated and the aqueous layer was reextracted with a second volume of ethyl acetate. The two ethyl acetate extracts were pooled, and concentrated under reduced pressure to an oil. The resulting crude extract (98 g) was dissolved in n-hexane and extracted twice with acetonitrile. Partial crystallization at this step yielded the mixed salt of antibiotix X-14885A. Mp. 290°–292° C.

Step B. The pooled acetonitrile extract of Step A was concentrated to an oil, dissolved in methylene chloride washed sequentially with equal volumes of 1 N HCl, saturated sodium carbonate and water, and then was dried over sodium sulfate. After filtration and concentration to an oil, was crystallized from methylene chloride by the addition of diethyl ether. The crystals were washed with methyl alcohol and were recrystallized from acetone by the addition of water. The antibiotic crystallized as X-14885A-Na.H₂O. Mp. 264°–266° C. The structure of antibiotic X-14885A was determined by the X-ray analysis of this monohydrated sodium salt.

EXAMPLE 3

Preparation of the Na Salt of Antibiotic X-14885A

The mixed salt of antibiotic X-14885A was dissolved in methylene chloride and was washed with 1 N HCl followed by saturated $Na_2CO_3$ and water. Solvent was removed under reduced pressure and crystallized from diethyl ether by the addition of hexane. Mp. 278° C.

EXAMPLE 4

Preparation of the Ca Salt of Antibiotic X-14885A

The mixed salt of antibiotic X-14885A was dissolved in methylene chloride and was washed with 1 N HCl, saturated $Ca(OH)_2$, water. Crystallization from acetone/hexane. Mp. 311° C.

EXAMPLE 5

Preparation of the Methyl Ester of Antibiotic X-14885A

A methylene chloride solution of the mixed salt of antiobiotic X-14885A was washed with 1 N HCl and dried by passing through a small celite column. The solvent was evaporated under reduced pressure and the residue dissolved in diethyl ether. This ethereal solution was chilled (by placing in an ice/methyl alcohol/salt bath) and freshly generated diazo methane was added in excess. The reaction mixture was allowed to warm up to room temperature, and the solvent was removed under reduced pressure. The structure of the methyl ester of antibiotic X-14885A was confirmed by mass spectrometry.

Antibiotic X-14885A has exhibited antimicrobial activity against a variety of gram positive bacterial as indicated in Table 4 below:

TABLE 4

| Microorganisms | ATCC No. | In Vitro Antimicrobial Spectrum Minimum Inhibitory Concentration (mcg/ml) of Antibiotic |
|---|---|---|
| G(+) Cocci | | |
| Streptococcus faecium | 8043 | 0.8 |
| Staphylococcus aureus | 6538p | 0.8 |
| Sarcina lutea | 9341 | 3.1 |
| G(+) Rods | | |
| Bacillus megaterium | 8011 | 0.4 |
| Bacillus Sp. E | 27859 | 0.2 |
| Bacillus subtilis | 558* | 0.2 |
| Bacillus Sp. Ta | 27860 | 0.4 |
| G(+) Filaments | | |
| Mycobacterium phlei | 355 | 3.9 |
| Streptomyces cellulosae | 3313 | 1.6 |

*NRRL No.

As indicated above antibiotic X-14885A and its salts possess the property of adversely affecting the growth of certain gram positive bacteria. They are useful in wash solutions for sanitary purposes as in the washing of hands and the cleaning of equipment, floors or furnishings of contaminated rooms or laboratories.

Antibiotic X-14885A also exhibits activity against *Treponema hyodysenteriae* a causative agent in swine dysentery. The antibiotic exhibits activity at 0.4 mcg/ml in in vitro screening.

Administration of antibiotic X-14885A as an antiswine dysentery agent is most easily accomplished by mixing it in the animal's feed.

However, the antibiotic can be usefully administered in other ways. For example, it can be incorporated into tablets, drenches, boluses or capsules and dosed to the animals. Formulation of the antibiotic compound in such dosage forms can be accomplished by means of methods well-known in the veterinary pharmaceutical art.

Capsules are readily produced by filling gelatin capsules with any desired form of the desired antibiotic. If desired, the antibiotic can be diluted with an inert powdered diluent, such as, sugar, starch, or purified crystalline cellulose in order to increase its volume for convenience in filling capsules.

Tablets of the antibiotic are made by conventional pharmaceutical processes. Manufacture of tablets is a well-known and highly advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface-active agents, such as, sodium lauryl sulfate and dioctyl sodium sulphosuccinate are also sometimes used. Commonly used absorbents again include starch and lactose while magnesium carbonate is also useful for oily substances. Frequently used binders are gelatin, gums, starch, dextrin and various cellulose derivatives. Among the commonly used lubricants are magnesium stearate, talc, paraffin wax, various metallic soaps, and polyethylene glycol.

The administration of the antibiotic compound may be as a slow-pay-out bolus. Such boluses are made as tablets except that a means to delay the dissolution of the antibiotic is provided. Boluses are made to release for lengthy periods. The slow dissolution is assisted by choosing a highly water-insoluble form of the antibiotic.

Dissolution of the antibiotic is delayed by use of a matrix of insoluble materials in which the drug is inbedded. For example, substances such as vegetable waxes, purified mineral waxes, and water-insoluble polymeric materials are useful.

Drenches of the antibiotic are preferred most easily by choosing a water-soluble form of the antibiotic. If an insoluble form is desired for some reason, a suspension may be made. Alternatively, a drench may be formulated as a solution in a physiologically acceptable solvent, such as, a polyethylene glycol.

Suspensions of insoluble forms of the antibiotic can be prepared in nonsolvents, such as, vegetable oils, such as, peanut, corn, or sesame oil, in a glycol, such as, propylene glycol or a polyethylene glycol; or in water, depending on the form of the antibiotic chosen.

Suitable physiologically acceptable adjuvants are necessary in order to keep the antibiotic suspended. The adjuvants can be chosen from among the thickeners, such as, carboxymethylcellulose, polyvinylpyrrolidone, gelatin, and the alginates. Many classes of surfactants serve to suspend the antibiotic. For exampe, lecithin, alkylphenol polyethylene oxide adducts, naphthalenesulfonates, alkylbenzenesulfonates, and the polyoxyethylene sorbitan esters are useful for making suspension in liquid nonsolvents.

In addition many substances which effect the hydrophilicity, density, and surface tension of the liquid can assist in making suspensions in individual cases. For example, silicone anti-foams, glycols, sorbitol, and sugars can be useful suspending agents.

The suspendable antibiotic may be offered as a suspension, or as a dry mixture of the antibiotic and adjuvants to be diluted before use.

The antibiotic may also be administered in the drinking water of the swine. Incorporation into drinking water is performed by adding a water-soluble or water-suspendable form of the antibiotic to the water in the proper amount. Formulation of the antibiotic for addition to drinking water follows the same principles as formulation of drenches.

The most practical way to treat animals with the antibiotic compound is by the formulation of the compound into the feed supply. Any type of feed may be mentioned with the antibiotic compounds, including common dry feeds, liquid feeds, and pelleted feeds.

The methods of formulating drugs into animal feeds are well-known. It is usual to make a concentrated drug premix as a raw material for medicated feeds. For example, typical drug premixes may contain from about one to about 400 grams of drug per pound of premix. The wide range results from the wide range of concentration of drug which may be desired in the final feed. Premixes may be either liquid or solid.

The formulation of swine feeds containing the proper amounts of antibiotic for useful treatment is well understood. It is necessary only to calculate the amount of compound which it is desired to administer to each animal, to take into account the amount of feed per day which the animal eats and the concentration of antibiotic compound in the premix to be used, and calculate the proper concentration of antibiotic compound, or of premix, in the feed.

What is claimed:

1. A process to produce a compound of the formula

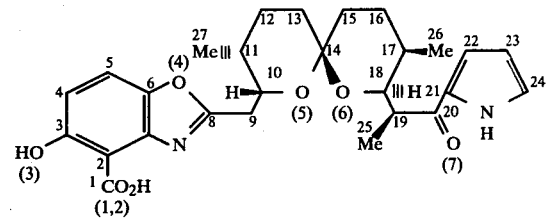

which comprises fermentatively cultivating a strain having the identifying characteristics of Streptomyces sp. X-14885 NRRL 12350 in an aqueous carbohydrate solution containing a nitrogenous nutrient under submerged aerobic conditions and thereafter isolating the product from said fermentation solution.

* * * * *